United States Patent
Bailly et al.

(10) Patent No.: US 11,672,636 B2
(45) Date of Patent: *Jun. 13, 2023

(54) PROSTHESIS FOR INGUINAL HERNIA REPAIR

(71) Applicant: SOFRADIM PRODUCTION, Trevoux (FR)

(72) Inventors: Pierre Bailly, Caluire-et-Cuire (FR); Mylene Desorme, Villeurbanne (FR); Suzelei Montanari, Trevoux (FR)

(73) Assignee: SOFRADIM PRODUCTION, Trevoux (FR)

( * ) Notice: Subject to any disclaimer, the term of this patent is extended or adjusted under 35 U.S.C. 154(b) by 435 days.

This patent is subject to a terminal disclaimer.

(21) Appl. No.: 16/895,888

(22) Filed: Jun. 8, 2020

(65) Prior Publication Data
US 2020/0297472 A1 Sep. 24, 2020

Related U.S. Application Data

(63) Continuation of application No. 15/965,826, filed on Apr. 27, 2018, now Pat. No. 10,675,137.

(30) Foreign Application Priority Data

May 2, 2017 (EP) ..................................... 17305489

(51) Int. Cl.
*A61F 2/00* (2006.01)

(52) U.S. Cl.
CPC .... *A61F 2/0063* (2013.01); *A61F 2002/0068* (2013.01); *A61F 2210/0004* (2013.01);
(Continued)

(58) Field of Classification Search
CPC ....................... A61F 2/0063; A61F 2230/0063
See application file for complete search history.

(56) References Cited

U.S. PATENT DOCUMENTS

| 1,187,158 A | 6/1916 | Mcginley |
| 3,054,406 A | 9/1962 | Usher |

(Continued)

FOREIGN PATENT DOCUMENTS

| CA | 1317836 C | 5/1993 |
| CN | 201879864 U | 6/2011 |

(Continued)

OTHER PUBLICATIONS

Communication pursuant to Article 94(3) EPC issued in European Application No. 17305489.1 dated Feb. 19, 2021, 6 pages.
(Continued)

*Primary Examiner* — Melanie R Tyson
(74) *Attorney, Agent, or Firm* — Weber Rosselli & Cannon LLP

(57) ABSTRACT

The present invention relates to methods of repairing an inguinal hernia defect including . . . a first portion forming a partial spherical cap surface shaped and dimensioned . . . a second portion extending from an inferior edge of the first portion . . . characterized in that the piece further includes: a third portion forming an arched part extending longitudinally in the inferior direction from a medial inferior corner of the first portion, the arched part extending radially substantially in the front direction, the third portion being intended to face the medial inferior area of the inguinal anatomy, and introducing the prosthesis into a patient.

20 Claims, 4 Drawing Sheets

(52) U.S. Cl.
CPC ............... *A61F 2210/0071* (2013.01); *A61F 2230/0004* (2013.01); *A61F 2230/0023* (2013.01); *A61F 2230/0063* (2013.01); *A61F 2240/001* (2013.01); *A61F 2250/0018* (2013.01)

(56) References Cited

U.S. PATENT DOCUMENTS

| | | |
|---|---|---|
| 3,118,294 A | 1/1964 | Laethem |
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schäfer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,840,629 A | 6/1989 | Bustos |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,071,433 A | 12/1991 | Naestoft et al. |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,584,884 A | 12/1996 | Pignataro |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |

(56) References Cited

U.S. PATENT DOCUMENTS

| | | |
|---|---|---|
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,954,767 A | 9/1999 | Pajotin et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D Aversa et al. |
| 6,113,623 A | 9/2000 | Sgro |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Robert |
| 6,334,872 B1 | 1/2002 | Termin et al. |
| 6,368,541 B1 | 4/2002 | Pajotin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Mueller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Bryan et al. |
| 6,723,133 B1 | 4/2004 | Pajotin |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,740,122 B1 | 5/2004 | Pajotin |
| 6,743,435 B2 | 6/2004 | Devore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B2 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |

(56) References Cited

U.S. PATENT DOCUMENTS

| | | |
|---|---|---|
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,476,249 B2 | 1/2009 | Frank |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,372 B2 | 3/2010 | Shfaram et al. |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 3,007,531 A1 | 8/2011 | Frank |
| 7,998,152 B2 | 8/2011 | Frank |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,506,627 B2 | 8/2013 | Van et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,728,159 B2 | 5/2014 | Kim et al. |
| 8,734,471 B2 | 5/2014 | Deitch |
| 8,746,014 B2 | 6/2014 | Mortarino |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 9,346,791 B2 | 5/2016 | Liu et al. |
| 9,713,519 B2 | 7/2017 | Horton et al. |
| 9,931,198 B2 | 4/2018 | Doucet et al. |
| 10,675,137 B2 * | 6/2020 | Bailly .................. A61F 2/0063 |
| 2002/0087174 A1 | 7/2002 | Capello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0036266 A1 | 2/2006 | Sulamanidze et al. |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0082864 A1 | 3/2009 | Chen et al. |
| 2009/0105526 A1 | 4/2009 | Piroli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |

(56) References Cited

U.S. PATENT DOCUMENTS

| | | |
|---|---|---|
| 2009/0216338 A1 | 8/2009 | Gingras et al. |
| 2009/0270999 A1 | 10/2009 | Brown |
| 2009/0281558 A1 | 11/2009 | Li et al. |
| 2009/0318752 A1 | 12/2009 | Evans et al. |
| 2010/0104608 A1 | 4/2010 | Abuzaina et al. |
| 2010/0130814 A1* | 5/2010 | Dubernard ............ A61F 2/0045 600/30 |
| 2010/0137679 A1 | 6/2010 | Lashinski et al. |
| 2010/0318108 A1* | 12/2010 | Datta ................... A61L 31/146 156/60 |
| 2011/0015760 A1 | 1/2011 | Kullas |
| 2011/0054604 A1 | 3/2011 | Becker |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet et al. |
| 2011/0257666 A1 | 10/2011 | Ladet et al. |
| 2011/0257761 A1 | 10/2011 | Mortarino |
| 2012/0004723 A1 | 1/2012 | Mortarino et al. |
| 2012/0016388 A1 | 1/2012 | Houard et al. |
| 2012/0029537 A1 | 2/2012 | Mortarino |
| 2012/0053690 A1 | 3/2012 | Frank |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2012/0226352 A1 | 9/2012 | Becker |
| 2012/0283826 A1 | 11/2012 | Moses et al. |
| 2013/0178875 A1 | 7/2013 | Horton et al. |
| 2013/0253645 A1 | 9/2013 | Kerr et al. |
| 2014/0044861 A1 | 2/2014 | Boey et al. |
| 2014/0100656 A1 | 4/2014 | Namnoum et al. |
| 2014/0276993 A1 | 9/2014 | Reilly et al. |
| 2014/0364684 A1 | 12/2014 | Lecuivre et al. |
| 2016/0051357 A1* | 2/2016 | Bailly ................... A61F 2/0063 600/37 |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1216717 A1 | 6/2002 |
| EP | 1216718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| EP | 3000432 A1 | 3/2016 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2612392 A1 | 9/1988 |
| FR | 2682284 A1 | 4/1993 |
| FR | 2715309 A1 | 7/1995 |
| FR | 2715405 A1 | 7/1995 |
| FR | 2724563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 B1 | 12/2005 |
| FR | 2876020 A1 | 4/2006 |
| FR | 2863277 B1 | 6/2006 |
| FR | 2884706 B1 | 4/2008 |
| FR | 2929834 A1 | 10/2009 |
| FR | 2953709 A1 | 6/2011 |
| GB | 1174814 A | 12/1969 |
| GB | 2051153 A | 1/1981 |
| GB | 2306110 A | 4/1997 |
| JP | H0332677 U | 3/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| NZ | 563828 A | 9/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9310731 A1 | 6/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |

(56) References Cited

FOREIGN PATENT DOCUMENTS

| WO | 0180773 A1 | 11/2001 |
|---|---|---|
| WO | 0181667 A1 | 11/2001 |
| WO | 0207648 A1 | 1/2002 |
| WO | 0217853 A2 | 3/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004096098 A1 | 11/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023414 A1 | 3/2006 |
| WO | 2007004214 A2 | 1/2007 |
| WO | 2008066883 A2 | 6/2008 |
| WO | 2009039373 A1 | 3/2009 |
| WO | 2009071998 A2 | 6/2009 |
| WO | 2009031035 A3 | 1/2010 |
| WO | 2010043978 A2 | 4/2010 |
| WO | 2007048099 A3 | 9/2010 |
| WO | 2011007062 A1 | 1/2011 |
| WO | 2011026987 A1 | 3/2011 |
| WO | 2011038740 A1 | 4/2011 |
| WO | 2014041577 A1 | 3/2014 |

OTHER PUBLICATIONS

Chinese Office Action issued in Chinese Application No. 201810386483.1 dated Apr. 2, 2021 with English Translation.
Amid, P., "Lichtenstein tension-free hernioplasty: Its inception, evolution, and principles," Hernia, 2004; pp. 1-7, 8, published online Sep. 2003.
Blondin, C. et al. "Relationships between chemical characteristics and anticomplementary activity of fucans," Biomaterials, Mar. 1996, pp. 597-603, 17(6).
Blondin, C. et al., "Inhibition of Complement Activation by Natural Sulfated Polysaccharides (Fucans) from Brown Seaweed," Molecular Immuol., Mar. 1994, pp. 247-253, 31(4).
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Chen, G. et al., "A Hybrid Network of Synthetic Polymer Mesh and Collagen Sponge," The Royal Society of Chemistry 2000, Chem. Commun., Jul. 2000, pp. 1505-1506.
Collins, R. et al., "Use of collagen film as a dural substitute: Preliminary animal studies," Journal of Biomedical Materials Research, Feb. 1991, pp. 267-276, vol. 25.
Dr. S. Raz, "The Karl Mayer Guide to Tehnical Textiles," Jan. 2000, pp. 1-36, Obertshausen, Germany.
European Search Report for EP 15305634.6 dated Nov. 2, 2015 (3 pages).
European Search Report for EP17305489.1 dated Oct. 25, 2017 (3 pages).
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, 7 pp. 189-201, 52(2),published online Nov. 2009.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).
Hirano, S. et al., "The blood biocompatibility of chitosan and N-acylchitosans," J. Biomed. Mater. Res., Apr. 1985, 413-417, 19.
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Langenbech, M. R. et al., "Comparison of biomaterials in the early postoperative period," Surg Endosc., May 2003, pp. 1105-1109, 17 (7).
Logeart, D. et al., "Fucans, sulfated polysaccharides extracted from brown seaweeds, inhibit vascular smooth muscle cell proliferation. IL Degradation and molecular weight effect," Eur. J. Cell. Biol., Dec. 1997, pp. 385-390, 74(4).
Malette, W. G. et al., "Chitosan, A New Hemostatic," Ann Th. Surg., Jul. 1983, pp. 55-58, 36.
Muzzarelli, R. et al., "Reconstruction of parodontal tissue with chitosan," Biomaterials, Nov. 1989, pp. 598-604, 10.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440, 11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004,pp. 211-220,18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva, T. et al., "Inhibition of complement activation by water-soluble polysaccharides of some far-eastern brown seaweeds," Comparative Biochem and Physiol, Jul. 2000, pp. 209-215,126(3).

* cited by examiner

PROSTHESIS FOR INGUINAL HERNIA REPAIR

CROSS-REFERENCE TO RELATED APPLICATIONS

This application is a continuation of U.S. patent application Ser. No. 15/965,826 filed Apr. 27, 2018, which claims benefit of and priority to European Patent Application No. 17305489.1 filed May 2, 2017, the disclosures of each of the above-identified applications are hereby incorporated by reference in their entirety.

BACKGROUND

The present invention relates to a preformed three-dimensional prosthesis to be used for repair of inguinal hernias.

SUMMARY

In this application, the "medial" end or part of an element of a prosthesis is to be understood as meaning the end or part of the element located in the direction of the median plane of the body when the prosthesis is implanted in the body. The "lateral" end or part of an element of a prosthesis is to be understood as meaning the end or part of the element located in the direction of the outwards lateral plane of the body when the prosthesis is implanted in the body. Likewise, in this application, the "medial direction" is to be understood as meaning the direction towards said median plane and the "lateral direction" is opposite the "medial direction", the medial and lateral directions being aligned on the same axis, the medial-lateral axis. In this application, the "superior" end or part of an element of a prosthesis is to be understood as meaning the end or part of the element located substantially in the direction of the head of the body when the prosthesis is implanted in the body. The "inferior" end or part of an element of a prosthesis is to be understood as meaning the end or part of the element located in the direction of the feet of the body when the prosthesis is implanted in the body. Likewise, in this application, the "superior direction" is to be understood as meaning the direction towards said head and the "inferior direction" is opposite the "superior direction", the superior and inferior directions being aligned on the same axis, the superior-inferior axis. In this application, the "front" end or part of an element of a prosthesis is to be understood as meaning the end or part of the element located substantially in the direction of the front of the body when the prosthesis is implanted in the body. The "rear" end or part of an element of a prosthesis is to be understood as meaning the end or part of the element located in the direction of the back of the body when the prosthesis is implanted in the body. Likewise, in this application, the "front direction" is to be understood as meaning the direction towards said front and the "rear direction" is opposite the "front direction", the front and rear directions being aligned on the same axis, the front-rear axis.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias, depending on where they are located.

Wall reinforcement prostheses, for example for the abdominal wall, are widely used in surgery. These prostheses are intended to treat hernias by temporarily or permanently filling a tissue defect. These prostheses are generally made from a biocompatible prosthetic textile and can have a number of shapes, for example rectangular, circular or oval, depending on the anatomical structure to which they are to adapt. Some of these prostheses may show three-dimensional shapes.

Indeed, when an inguinal hernia is to be treated, it is of particular importance to take into account the anatomy of the inguinal region, in particular the presence of the iliac vessels. In addition, when the patient is a man, the spermatic cord needs to be taken into account while positioning the prosthesis. The various anatomical organs to be taken into account confer to the inguinal region to be treated a three-dimensional shape. In addition, the shape of the inguinal region being asymetric, the shape of a prosthesis intended to be used for treating an inguinal hernia will be dependent on the side (right or left) of the body that is to be treated. In this view, the shape of a prosthesis for treating an inguinal hernia may be defined in relation with the position of the prosthesis once implanted in the body of a patient. For example, in an implanted configuration, a three-dimensional prosthesis for treating an inguinal hernia may comprise a medial part, a lateral part, a superior part, an inferior part, a front part and a rear part as defined above.

With reference to FIG. 1, on which are indicated the medial-lateral axis A and the superior-inferior axis B, the anterior retro-parietal space of the inguinal region for the right hand side of a body is shown; in other words the inguinal region is shown from a view point located in the rear side of the body, for example from the interior of the abdominal cavity but with the peritoneum not shown on the Figure for sake of clarity, and looking towards the front side of the body, in other words in the direction of the abdominal skin of the body. On FIG. 1, one can see:

- in direction of the front side of the body, the rectus abdominis muscles 116 and the transverse muscle 118 forming part of the anterior abdominal wall of the abdomen,
- in the direction of the lateral side of the body, the psoas muscle 112, the iliac vessels 111, and the elements of the spermatic cord 120,
- in the direction of the medial inferior side of the body, the upper part of the pubic bone 117.

On FIG. 1, are represented in dotted lines the three locations for potential hernias to occur in the inguinal region: the indirect inguinal hernia, shown as dotted line circle 122 on FIG. 1, occurs mainly in the lateral area of the inguinal region: it is a swelling of the groin caused when a portion of the peritoneum (not shown but located between the FIG. 1 and the person looking at FIG. 1), possibly containing abdominal viscera, passes through the orifice of the inguinal canal. It is necessary to push the peritoneum, and possibly the abdominal viscera, back in the direction of the abdominal cavity, and place a barrier, namely a prosthesis, between the peritoneum and the orifice of the inguinal canal. The direct hernia, shown as dotted line circle 119 on FIG. 1, occurs mainly in the medial area of the inguinal region. The femoral hernia, shown as dotted line circle 121 on FIG. 1, occurs mainly in the medial inferior area of the inguinal region.

It will be noted in FIG. 1 that the elements described above are not all in the same spatial plane, but instead are arranged in an oblique arrangement from a superior-lateral corner to an inferior-medial corner. In the case of an inguinal hernia, the prosthesis implanted after reduction of the hernia must ensure satisfactory covering of the hernia to be treated, either direct, indirect or femoral, by adapting to the contours of the region and by respecting the obliqueness of the inguinal region, if possible without leaving any empty spaces.

When operating by laparoscopy for repairing an inguinal hernia, two routes may be used for bringing the prosthesis to the implantation site, namely the inguinal region. For example, according to a first surgical method, namely the transabdominal preperitoneal route (TAPP), the prosthesis is first conveyed to the abdominal cavity via a trocar; the peritoneum is then open and the prosthesis is brought to the inguinal region through the incision performed through the peritoneum. The peritoneum is closed once the implantation is completed. According to a second surgical method, namely the totally extra-peritoneal route (TEP), the prosthesis is brought to the inguinal region through a trocar directly through the muscles of the abdominal wall, and the peritoneum is not open.

Because of the obliqueness of the inguinal region and the restricted deployment space, it can prove complicated to deploy the prosthesis and then orient it suitably with respect to the orifice of the inguinal canal or to the other organs to be protected, such as the illiac vessels or the spermatic cord.

The effectiveness of the prosthesis, hence the ability to minimize the risks of recurrence, depends to a large extent on how well the prosthesis is correctly spread out against the biological tissues of the inguinal region. In the present application, "biological tissues of the inguinal region" are understood as the biological tissues of the organs or elements of the inguinal region that are shown in FIG. 1 and that are intended to be protected from the peritoneum with a view to repairing the hernia, and in particular the anterior muscle wall, the upper part of the pubic bone, the iliac and spermatic vessels, and part of the psoas muscle.

Indeed, prostheses based on a textile are generally flexible. In order to introduce them into a trocar, they are often folded up or rolled to reduce their volume. They therefore tend to form creases when introduced at the implantation site. The spreading out of textile based prosthesis from the trocar is of key importance but can prove difficult.

Document U.S. Pat. No. 6,723,133 describes a preformed three-dimensional prosthesis for the repair of inguinal hernia intended to conform to the anatomical shape of the defective wall. The prosthesis described in this patent comprises a plurality of distinctly shaped portions joined to each other, all said shaped portions being configured with a substantially spherical shape.

As seen above, the anatomy of the inguinal region implies various organs such as muscles having various shapes, vessels, such as the illiac vessels, having various paths, and the pubic bone. In addition, the anatomy of the inguinal region may vary significantly from one human being to the other, in particular in its medial inferior area, in the surroundings of the upper part of the pubic bone. It has been observed that, with some preformed three-dimensional prostheses of the prior art, this medial inferior area of the inguinal region is not covered efficiently. In particular, depending on the true anatomy of the patient being treated, the surgeon may need to apply a certain tension on the prosthesis or shift the prosthesis at the moment of positioning the prosthesis, so that a part of the prosthesis be present in the medial inferior area of the inguinal region, namely in the surroundings of the pubic bone. Alternatively the surgeon may need to create folds in the prosthesis so as to conform it to the specific shape of the medial inferior area of the inguinal region he is confronted to in relation with the patient he is treating.

There is therefore still the need for a prosthesis for repair of inguinal hernias that is based on a preformed three-dimensional piece of biocompatible material intended to globally conform to the anatomical shape of the defective wall in the inguinal region, that is able to be spread out from the trocar and cover efficiently not only said defective wall but also the medial inferior area of the inguinal region, whatever the true anatomical shape of said medial inferior area in the patient to be treated, such that the surgeon does not have to apply specific tensions on the prosthesis or create folds when positioning the prosthesis with respect to the biological tissues.

The present invention aims to meet such a need.

A first aspect of the invention is an implantable prosthesis for repairing a hernia defect in an inguinal region of a human body delimited by the anterior abdominal wall, the psoas muscle and a medial inferior area of the inguinal anatomy, the prosthesis comprising:

a piece of biocompatible material having a preformed three-dimensional shape, the piece including:

a first portion, intended to face the anterior abdominal wall, said first portion forming a partial spherical cap surface shaped and dimensioned so as to substantially conform to the shape of the anterior abdominal wall, a second portion, intended to face the psoas muscle, said second portion extending from an inferior edge of said first portion and forming a wavy-shaped wall, shaped and dimensioned so as to substantially conform to the shape of the psoas muscle, characterized in that said piece further comprises:

a third portion forming an arched part, said arched part extending longitudinally substantially in the inferior direction from a medial inferior corner of said first portion, said arched part extending radially substantially in the front direction, said third portion being intended to face the medial inferior area of the inguinal anatomy.

The prosthesis of the invention has a shape allowing it to conform ideally to the anatomy of the inguinal region to be reinforced. In particular, the shape and dimension of the first, second and third portions allow adapting the prostheses to different types of inguinal hernia, such as the direct inguinal hernia, the indirect inguinal hernia and the femoral inguinal hernia.

Moreover, the presence of the third portion of the prosthesis of the invention and the specific shape of this third portion allow covering the medial inferior area of the inguinal anatomy, in particular the region around the upper part of the pubic bone, without having to tear or stretch the other parts of the prosthesis or to create additional folds likely to undesirably interfere with the surrounding organs. Indeed, the presence of this third portion and its shape allow the surgeon to easily lay the entire prosthesis on each anatomical element to be protected without having to apply a particular compensating force on another part of the prosthesis or to shift the prosthesis. The prosthesis is perfectly spread out in the three dimensions of the inguinal region to be repaired, with no need to create folds in the prosthesis in order to conform it to the shape of the anatomy to be protected. There is no tension created in the prosthesis when it is positioned.

The prosthesis of the invention is intended to be used for repairing a hernia defect in the inguinal region of a human body. The prosthesis of the invention is particularly adapted for use in laparoscopic surgery, either via the transabdominal preperitoneal route (TAPP) or the totally extra-peritoneal route (TEP).

The inguinal region may be delimited by the anterior abdominal wall, the psoas muscle and a medial inferior area of the inguinal anatomy, in the surroundings of the pubic bone.

The prosthesis of the invention comprises a piece of biocompatible material having a preformed three-dimensional shape. The piece of biocompatible material comprises several portions, each having a determined shape, the assembly of these determined shapes forming the preformed three-dimensional shape. The piece of biocompatible material is preferably made as a unitary structure.

In the present application, "biocompatible" is understood as meaning that the materials having this property can be implanted in the human or animal body.

Biocompatible materials for forming hernia repair prosthesis are well known in the art. For example, the biocompatible material may comprise a bioresorbable, a non-bioresorbable material and mixtures thereof.

In the present application, "bioresorbable" or "biodegradable" is understood to mean that the materials having this property are absorbed and/or degraded by the tissues or washed from the implantation site and disappear in vivo after a certain time, which may vary, for example, from a few hours to a few years, depending on the chemical nature of the materials.

Examples of bioresorbable material suitable for the piece of the prosthesis of the invention can be chosen from among the following bioresorbable materials: polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), polyethylene glycol (PE), copolymers of these materials, and mixtures thereof.

Examples of non-bioresorbable material suitable for the piece of the prosthesis of the invention can be chosen from among the following non-bioresorbable materials: polypropylenes, polyesters such as polyethylene terephthalates, polyamides, silicones, polyether ether ketone (PEEK), polyarylether ether ketone (PAEK) and mixtures thereof.

The piece may be made from a preformed sheet of foam, preferably a porous material. Within the meaning of the present application, "porous material" is understood as a material having pores, voids or holes, that are open and are distributed uniformly or irregularly and promote cell colonization and tissue ingrowth. The pores can be present in all types of configurations, for example as spheres, channels, hexagonal forms.

In embodiments, the piece of biocompatible material comprises a textile, in particular a porous textile. In embodiments, the piece of biocompatible material consists in a textile, for example a porous textile.

According to the present invention, "textile" is understood as any arrangement or assembly of biocompatible yarns, fibres, filaments and/or multifilaments, for example obtained by knitting, weaving, braiding, or non-woven. Biocompatible textiles, in particular porous textiles, suitable for the repair of a hernia defect are well known in the art.

The piece of biocompatible material of the prosthesis of the invention comprises a first portion forming a partial spherical cap surface. The partial spherical cap surface is intended to face the anterior abdominal wall. The partial spherical cap surface may extend in the front direction, namely towards the abdominal wall. The partial spherical cap surface is shaped and dimensioned so as to conform to the shape of the anterior abdominal wall. A spherical cap suitable for forming said first portion may derive from a sphere having a diameter ranging from about 200 mm to about 220 mm, preferably ranging from about 206 mm to about 215 mm, said spherical cap having a height ranging from about 15 mm to about 35 mm, preferably from about 20 mm to about 28 mm. The partial spherical cap suitable for obtaining the surface forming the first portion may result from the removal of an inferior part of the spherical cap along a wavy line forming an inferior edge of the first portion.

The piece of biocompatible material of the prosthesis of the invention comprises a second portion forming a wavy-shaped wall intended to face the psoas muscle. The wavy-shaped wall extends from the inferior edge of the first portion and is shaped and dimensioned so as to conform to the shape of the psoas muscle. In embodiments, the wavy-shaped wall extends substantially from a lateral side to a medial side of the piece of biocompatible material and it includes a surface generated by a generatrix, under the form of a straight line D, following a directrix, under the form of a directing curved line C. In embodiments, the directing curved line C includes at least a lateral curve extending substantially in the inferior direction and at least a central curve, offset in the medial direction with respect to said lateral curve, said central curve extending substantially in the superior direction. In embodiments, the directing curved line C further includes a medial curve extending substantially in the inferior direction. The presence or not of the medial curve may depend on the anatomy of the patient to be treated, in particular on the size of the hernia defect to be repaired.

For example, the radius of curvature of the lateral curve may range from about 50 mm to about 55 mm, and may preferably be about 53 mm, the radius of curvature of the central curve may range from about 20 mm to about 35 mm, and may preferably be from about 24 mm to about 31 mm, and the radius of curvature of the medial curve, when present, may range from about 70 mm to about 90 mm, and may preferably be about 80 mm.

The wavy-shaped wall is preferably inclined with respect to the direction of the height of the spherical cap of the first portion. In embodiments, the angle formed between the generatrix of the wavy-shaped wall and the direction of the height of the spherical cap of the first portion may range from about 35° to about 50°, preferably from about 40° to about 45°.

The piece of biocompatible material further comprises a third portion forming an arched part. The arched part extends longitudinally substantially in the inferior direction from a medial inferior corner of said first portion, said arched part extending radially substantially in the front direction, said third portion being intended to face the medial inferior area of the inguinal anatomy. By "arched part" is meant in the present application an angular section of a tube. The radius of the arched part according to the present application is the radius of the tube from which the arched part derives.

In embodiments, the arched part has a radius ranging from about 70 mm to about 110 mm, preferably from about 80 mm to about 100 mm. In embodiments, the arched part extends circumferentially along a portion of a circle forming an angle ranging from about 30° to about 45°, preferably ranging from 33° to 40°. The arched part may have a height ranging from about 20 mm to about 40 mm, preferably from about 21 mm to about 35 mm. The arched part may have a length ranging from about 40 mm to about 60 mm, preferably from about 45 mm to about 53 mm.

The arched part allows covering the various organs present in the medial inferior area of the inguinal region. In particular, the shape and dimension of the arched part allow spreading easily the prosthesis without having to tear it or to create specific folds in order to adapt to the unique anatomy of the patient to be treated.

In embodiments, the height of the arched part is greater or equal, preferably greater, than the height of the spherical cap of the first portion. The arched part is therefore allowed to cover the medial inferior area of the inguinal region while the spherical cap conforms to the shape of the anterior abdominal wall, without having to apply any specific tension on the prosthesis in the front or rear directions.

In embodiments, said preformed three-dimensional shape defining an edge of said piece, said edge extends in the three dimensions of the space. The edge of the piece of biocompatible material follows the anatomy of the region to be protected in an optimum way. In particular, thanks to the fact that the edge of the piece extends in the three dimensions of the space, there is no need for the surgeon to create additional folds of the prosthesis in order to conform it to the anatomic shape to be protected.

In embodiments, said preformed three-dimensional shape defining an edge of said piece, said edge is provided with a reinforcement member at least on a part of its perimeter. The reinforcement member may be made from any biocompatible material and may run continuously or discontinuously along the edge. The reinforcement member may be selected from a moulded material, a wire, a fused textile part and combinations thereof. The reinforcement member is usually provided with a rigidity superior to that of the piece of biocompatible material and may help the handling of the prosthesis during the surgical operation.

In embodiments, the reinforcement member shows no elasticity along the perimeter of the edge. In other words, if one holds the piece at two points of its edge located substantially on a linear section of said edge, and tries to draw away one point from the other, the reinforcement member will show no elongation between the two points. The reinforcement member may therefore constitute a sort of three-dimensional non-elastic belt maintaining the edge of the piece of biocompatible material, where such belt provides a pop-up effect at the time the prosthesis comes out of a trocar for example. The reinforcement member therefore contributes to a more efficient deployment of the prosthesis when it comes out of the trocar.

In embodiments, the piece of biocompatible material may show an elasticity allowing it to be deformed when submitted to an outer pressure and to come back to its initial predetermined three-dimensional shape when said outer pressure is released. The surgeon may therefore be able to reduce the global volume of the prosthesis by applying an outer pressure on the prosthesis so as to fold it on itself at the time he introduces the prosthesis in the trocar. When the prosthesis is released from the trocar on the implantation site, namely in the inguinal region, the prosthesis comes naturally to its initial spread out three-dimensional shape.

A piece of biocompatible material showing such an elasticity may be made from a porous foam.

Alternatively, some textiles may form biocompatible material showing such an elasticity. A textile suitable for forming the piece of the prosthesis of the invention and showing an elasticity allowing it to be deformed when submitted to an outer pressure and to come back to its initial predetermined three-dimensional shape when said outer pressure is released is described in U.S. Pat. No. 6,478,727. For example, such a textile may comprise a porous knit made of polypropylene monofilament yarn having a diameter ranging from about 0.12 mm to about 0.25 mm, preferably from about 0.15 mm to about and 0.20 mm, for example of about 0.18 mm, and threaded one full one empty in two guide bars according to the following knitting pattern according to ISO 11676 standard, publication 2014: Bar I: 3-2/2-1/0-1//, Bar II: 0-1/1-2/3-2//. For example, the number of stitches per centimeter for such a porous knit may vary from about 7 to 15, preferably from about 10 to 12.

In embodiments, the reinforcement member comprises a fused part of a contour of the textile forming the piece of biocompatible material. Alternatively, the reinforcement member may consist in a fused part of a contour of said textile. The fused part of the contour of a textile allows forming a reinforcement member having a smooth outer shape and free of any potential traumatic part. The fused part of the contour of a textile further allows forming a reinforcement member showing no elasticity along the perimeter of the edge. The fused part of the contour of the textile also allows avoiding the self-gripping of the textile.

The contour of the textile may be fused via thermal welding, such as thermal impulse sealing, ultrasonic welding, or induction welding. For example, when thermal impulse sealing is used, the contour of the textile is compressed between two jaws and heated to the melting point of the material forming the textile.

In embodiments, a medial inferior part of the edge is free of any reinforcement member. The absence of any reinforcement member at the medial inferior part of the edge of the piece of the prosthesis of the invention allows the surgeon to freely direct and position the medial inferior part of the prosthesis in function of the shape of the anatomical organs located in the area of the medial inferior area of the inguinal region. Indeed, it is known that the anatomy of the medial inferior area of the inguinal region varies significantly from one human being to the other. Leaving the medial inferior part of the prosthesis free of any reinforced edge enables the surgeon to adapt the positioning and to customize the fixation of the prosthesis in this area to the true shape of the anatomy encountered for a specific patient. The medial inferior part of the prosthesis is therefore more conformable to the anatomical relief encountered in the treated patient.

In embodiments, the piece of biocompatible material is a textile showing an elasticity allowing it to be deformed when submitted to an outer pressure and to come back to its initial predetermined three-dimensional shape when said outer pressure is released, having a reinforcement member which is a fused part of said textile, where the medial inferior part of the edge is free of any reinforcement member. Such embodiments allow having a non-elastic belt, formed by the reinforcement member, maintaining the prosthesis on the main part of its edge, while leaving the medial inferior part of the edge preserve its elasticity, coming from the elasticity of the textile it is made of. Such embodiments allow the surgeons to benefit from the elasticity of the medial inferior part of the edge of the textile in order to easily move the prosthesis in the medial inferior area of the inguinal region and to more freely adapt the position of the prosthesis to this specific part of the anatomy, while at the same time having a prosthesis that has enough global rigidity to be manipulated efficiently and to be spread out easily from the trocar.

In embodiments, the piece further includes a fourth portion extending from the superior-medial part of the first portion, said fourth portion forming a triangular part defining a superior-medial corner of the prosthesis, said corner forming an angle ranging from about 100° to about 120°, preferably from about 105° to about 115°, for example of about 110°. Such a fourth portion allows providing an indication to the surgeon for better positioning the prosthesis. In particular, such a fourth portion helps the surgeon to orientate the prosthesis with regards to the Linea Alba. In addition, the presence of the triangular part forming the fourth portion of the prosthesis allows increasing the surface of the prosthesis in the medial superior area of the inguinal region. Such embodiments are particularly preferred for direct inguinal hernia as they consequently provide additional reinforcement in said medial superior area.

The preformed three-dimensional shape of the prosthesis of the invention may be obtained using any preforming process known in the art, such as a compressive thermoforming process using a traditional two-parts mold. For example, a first part of the mold exhibits an outer surface having the desired shape for the piece of the prosthesis to be obtained and a second part of the mold has a shape similar to that of the first part but recessed into its inner surface. The sheet of biocompatible material, for example a textile, is then secured between the first and the second parts of the mold, the whole being heated at a temperature ranging from about 140° C. to about 150° C. and further cooled down. The preformed three-dimensional shaped piece thus obtained is removed from the mold.

BRIEF DESCRIPTION OF THE DRAWINGS

The present invention will become clearer from the following description and from the attached drawings, in which.

DETAILED DESCRIPTION OF EMBODIMENTS

Figure 1:
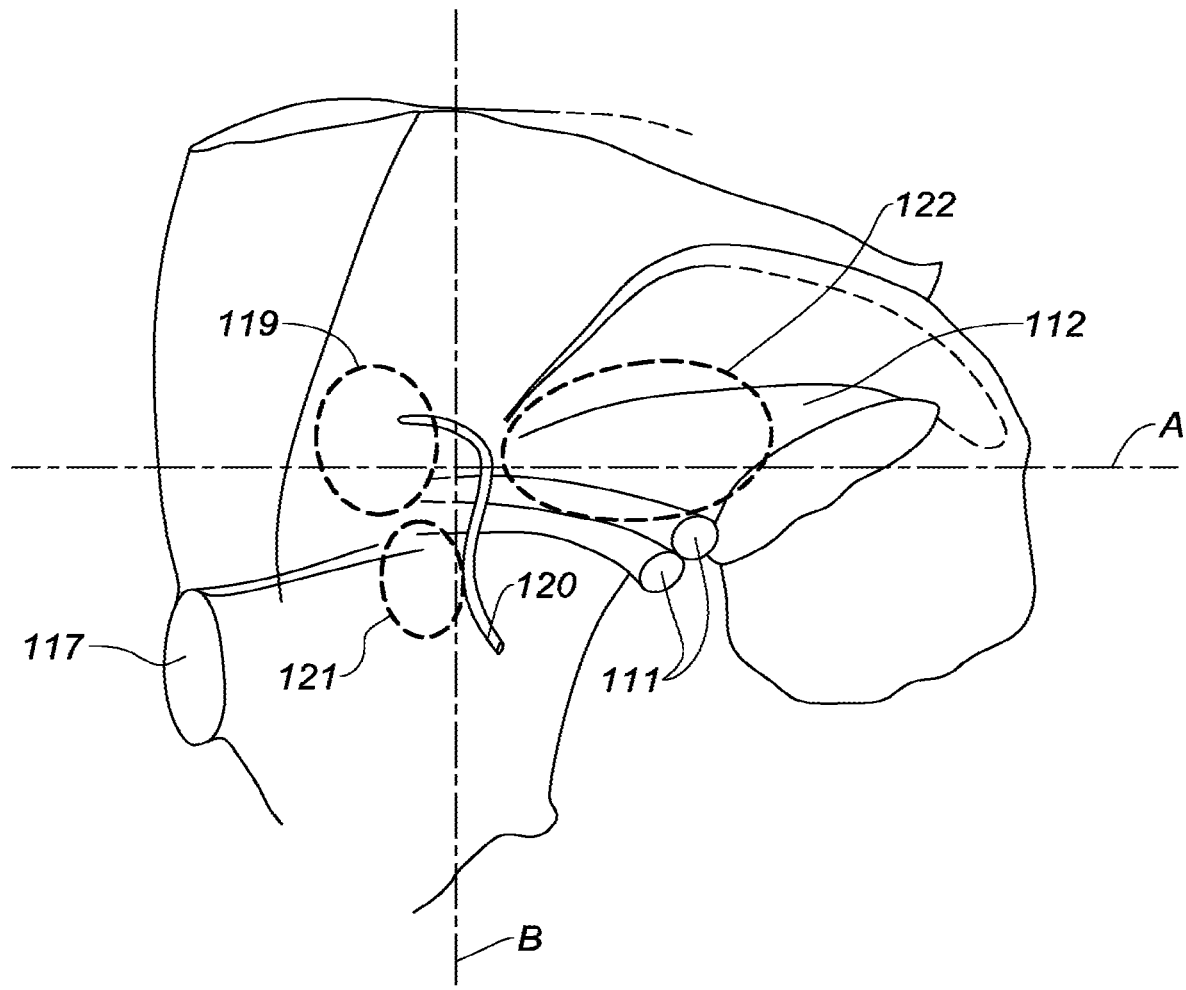
FIG. 1 is a schematic view of the inguinal region.
Figure 2A:
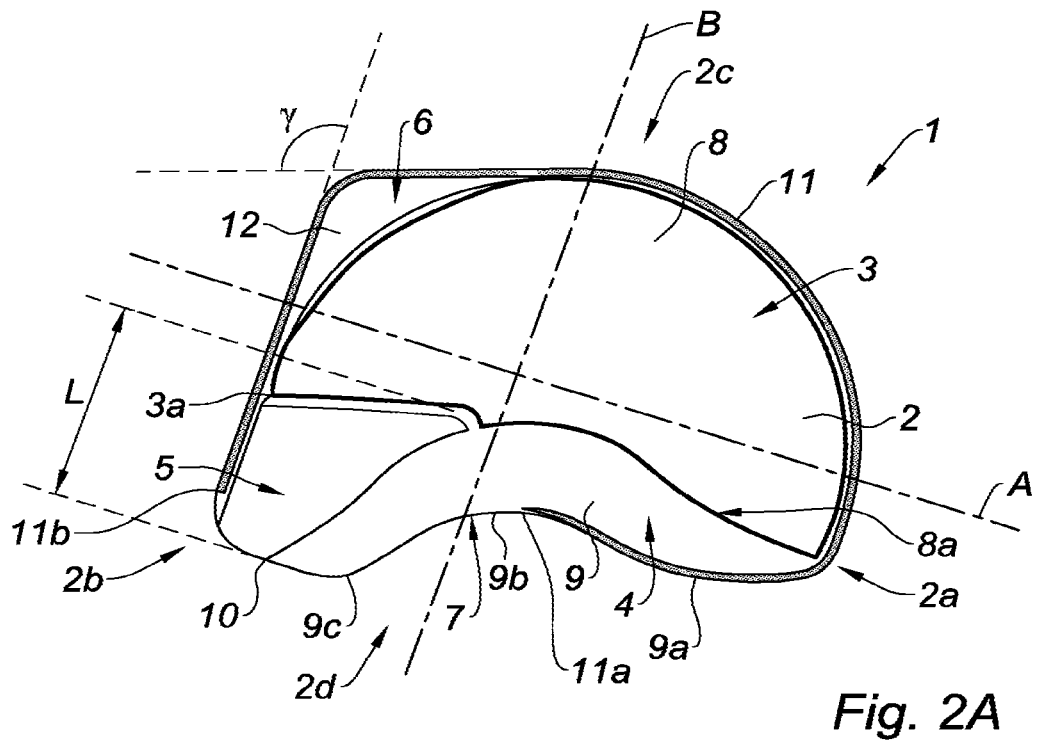
FIG. 2A is a top view of a first embodiment of a prosthesis of the invention.

With reference to FIG. 2A, is shown a prosthesis 1 of the invention for repairing a hernia defect in an inguinal region of the human body. The prosthesis 1 shown on FIG. 1 is intended to be implanted in the left hand side of a patient body. The prosthesis 1 comprises a piece 2 of biocompatible material having a preformed three-dimensional shape. On FIG. 2A are indicated the medial-lateral axis A and the superior-inferior axis B. The preformed piece 2 of FIG. 2A has a lateral side 2a, a medial side 2b, a superior side 2c and an inferior side 2d. On FIG. 2A is shown the front side of the prosthesis 1.

The piece 2 comprises a first portion 3, which is intended to face the anterior abdominal wall, a second portion 4, which is intended to face the psoas muscle and a third portion 5, which is intended to face the medial inferior area of the inguinal region. In the example shown the piece 2 further comprises a fourth portion 6, intended to ease the alignment of the prosthesis 1 on the Linea Alba. In embodiments not shown, the piece 2 does not comprise such fourth portion. The first portion 3, second portion 4, third portion 5 and fourth portion 6 are all united to form the preformed three-dimensional shaped piece 2 as a unitary structure. The piece 2 has an edge 7 defined by the contour of its preformed three-dimensional shape.

Each portion (3, 4, 5, 6) of the piece 2 of biocompatible material will now be described in detail.

The first portion 3 forms a partial spherical cap surface 8. The partial spherical cap surface 8 is intended to face the anterior abdominal wall once the prosthesis 1 is implanted in the body of a patient. The partial spherical cap surface 8 therefore extends in the front direction, namely towards the abdominal wall. The partial spherical cap surface 8 is shaped and dimensioned so as to conform to the curved shape of the anterior abdominal wall. The partial spherical cap surface 8 is further intended to be positioned adjacent the psoas muscle in an implanted configuration. In this view, the partial spherical cap surface 8 is derived from a spherical cap from which an inferior part has been removed, the inferior part removed corresponding to the presence of the psoas muscle. The partial spherical cap surface 8 may therefore be a spherical cap surface that has been cut in its inferior part along a line delimited by the shape of the psoas muscle. Such a line forms an inferior edge 8a of the partial spherical cap surface 8.

Figure 4:
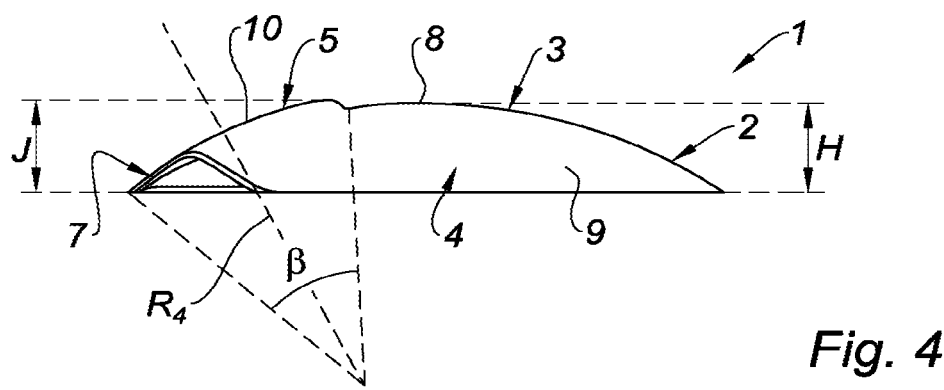
FIG. 4 is a side view of the prosthesis of FIG. 2A showing the radius of the arched part, the angle of the portion of a circle on which extends the arched part, and the height of the arched part.

The spherical cap from which the first portion 3 is formed may be obtained from the cutting of a cap from a sphere having a diameter ranging from about 200 mm to about 220 mm, preferably ranging from about 206 mm to about 215 mm, where the cut cap has a height H, as shown on FIG. 4, ranging from about 15 mm to about 35 mm, preferably from about 20 mm to about 28 mm. The partial spherical cap surface 8 forming the first portion 3 may result from the removal of an inferior part of such a spherical cap along a wavy line forming the inferior edge 8a of the partial spherical cap 8 and of the first portion 3.

The second portion 4 forms a wavy-shaped wall 9 intended to face the psoas muscle once the prosthesis 1 is implanted in the body of a patient. The wavy-shaped wall 9 extends from the inferior edge 8a of the first portion 3 and is shaped and dimensioned so as to conform to the shape of the psoas muscle.

With reference to FIG. 2A, the wavy-shaped wall 9 extends from a lateral side 2a to substantially a medial side 2b of the piece 2. The wavy-shaped wall 9 includes a surface generated by a generatrix, under the form of a straight line D shown for example on FIGS. 3A and 3B, following a directrix, under the form of a directing curved line C shown for example on FIG. 5. The wavy-shaped wall 9 may comprise a succession of several curves, for example two or three curves, forming a wave. In the example shown in FIG. 2A, the wavy-shaped wall 9 comprises three curves, namely a lateral curve 9a extending substantially in the inferior direction, a central curve 9b extending substantially in the superior direction and a medial curve 9c extending in the inferior direction.

Figure 5:
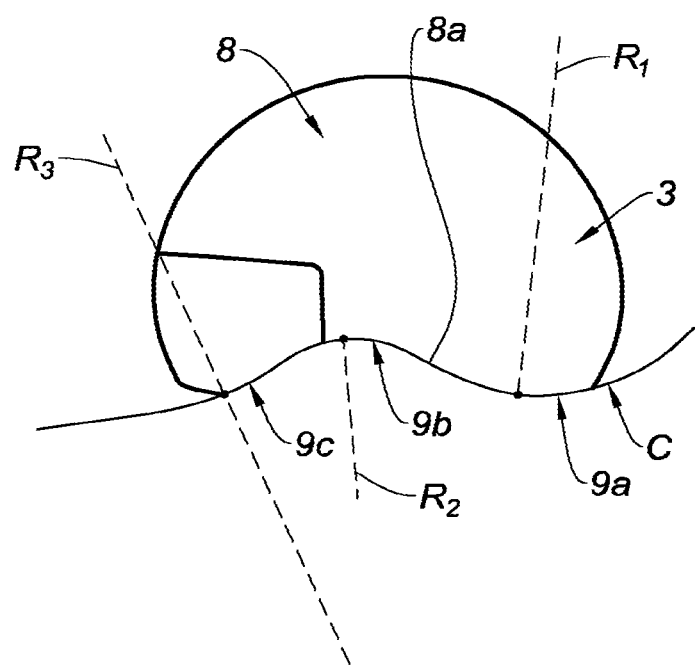
FIG. 5 is a schematic top view of the first portion of the prosthesis of FIG. 2A showing the radius of curvature of the curves of the wavy-shaped wall.

With reference to FIG. 5, is shown a schematic top view of the first portion 3 of FIG. 2A showing the directing curved line C including the lateral curve 9a, the central curve 9b and the medial curve 9c and their corresponding radius of curvatures (R1, R2, R3).

For example, the radius of curvature of the lateral curve 9a, shown as R1 on FIG. 5, may range from about 50 mm to about 55 mm, and may preferably be about 53 mm, the radius of curvature of the central curve 9b, shown as R2 on FIG. 5, may range from about 20 mm to about 35 mm, and may preferably be from about 24 mm to about 31 mm, and the radius of curvature of the medial curve 9c, shown as R3 on FIG. 5, may range from about 70 mm to about 90 mm, and may preferably be about 80 mm.

Figure 3A:
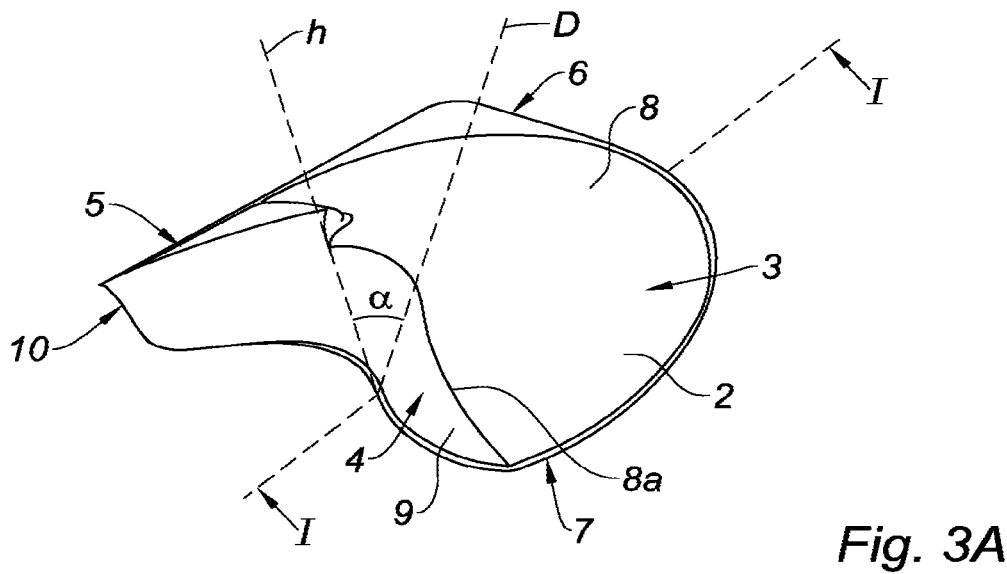
FIG. 3A is a side perspective view of the prosthesis of FIG. 2A.
Figure 3B:
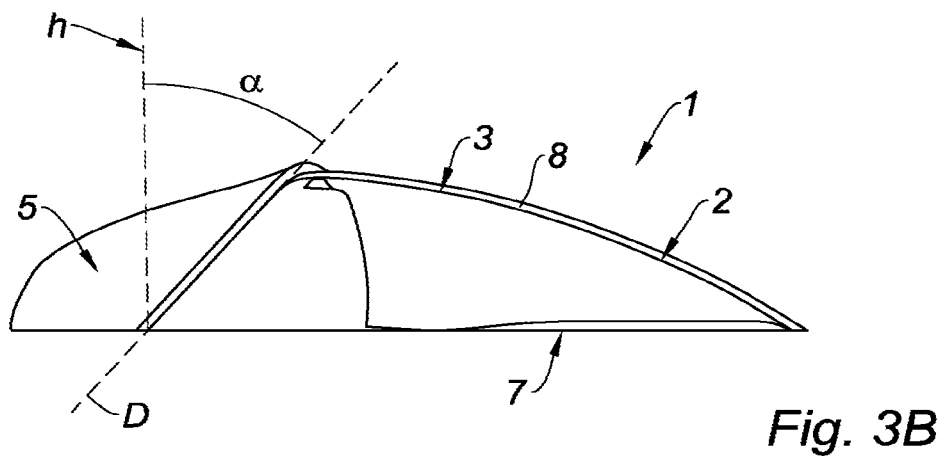
FIG. 3B is a cross section view of the prosthesis of FIG. 3A taken along line I-I, showing the angle between the direction of the height of the spherical cap and the generatrix of the wavy-shaped wall.

The wavy-shaped wall 9 is inclined with respect to the direction of the height "h" of the spherical cap 8 of the first portion 3. With reference to FIG. 3A and 3B, the angle α formed between the generatrix D of the wavy-shaped wall and the direction "h" of the height of the spherical cap surface 8 of the first portion 3 may range from about 35° to about 50°, preferably from about 40° to about 45°.

Figure 2B:
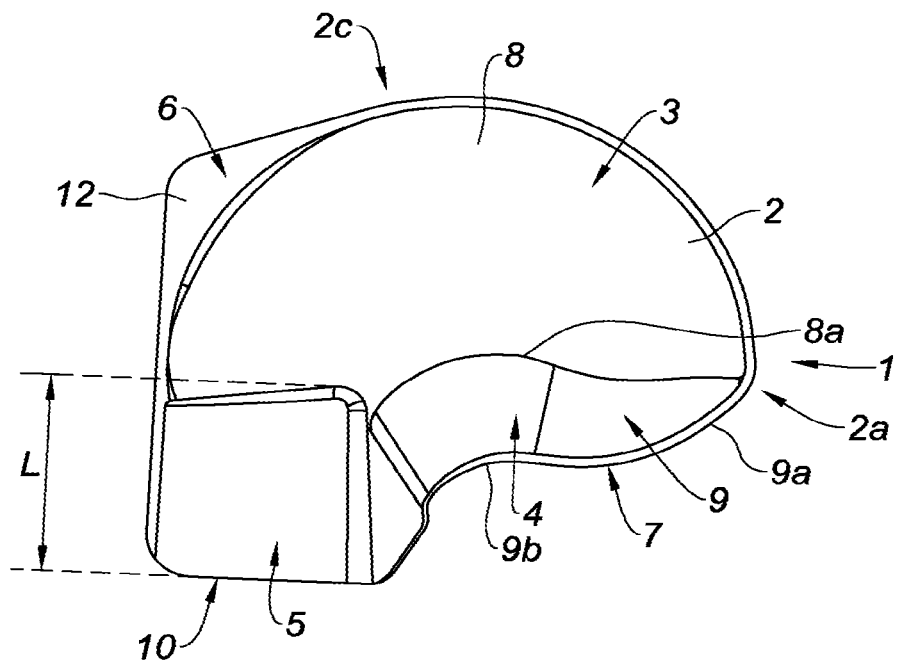
FIG. 2B is a top view of a second embodiment of the prosthesis of the invention.

With reference to FIG. 2B, is shown a second embodiment of the prosthesis 1 of FIG. 1, in which the wavy-shaped wall 9 does not comprise any medial curve. As will appear from the description below, the prosthesis of FIG. 2B may be designed for cases where the size of the hernia defect in the medial inferior area of the inguinal region requires high coverage from the prosthesis 1. The third portion 5 is made larger and replaces the medial curve of the wavy-shaped wall 9.

With reference to FIG. 2A, the third portion 5 forms an arched part 10. The arched part 10 extends longitudinally substantially in the inferior direction from a medial inferior corner 3a of the first portion 3. As better seen on FIG. 4, the arched part 10 extends radially substantially in the front direction.

The arched part 10 forming the third portion 5 is intended to face the medial inferior area of the inguinal anatomy. The radius R4 of the arched part 10 is the radius of the tube from which the arched part derives and is shown in FIG. 4.

The arched part 10 may have a radius R4 ranging from about 70 mm to about 110 mm, preferably from about 80 mm to about 100 mm.

With reference to FIG. 4, the arched part 10 extends circumferentially along a portion of a circle forming an angle β ranging from about 30° to about 45°, preferably ranging from 33° to 40°.

Still with reference to FIG. 4, the arched part 10 may have a height J ranging from about 20 mm to about 40 mm, preferably from about 21 mm to about 35 mm. With reference to FIGS. 2A and 2B, the arched part 10 may have a length L ranging from about 40 mm to about 60 mm, preferably from about 45 mm to about 53 mm.

The arched part 10 allows covering the various organs present in the medial inferior area of the inguinal region. In particular, the shape and dimension of the arched part 10 allow spreading easily the prosthesis 1 without having to tear it or to create specific folds in order to adapt to the unique anatomy of the patient to be treated.

Still with reference to FIG. 4, the height J of the arched part 10 is greater than the height H of the spherical cap of the first portion 3. Once the prosthesis 1 is implanted, the arched part 10 is thus allowed to cover the medial inferior area of the inguinal region while the spherical cap surface 8 conforms to the shape of the anterior abdominal wall, without having to apply any specific tension on the prosthesis in the front or rear directions.

With reference to FIG. 2A, the fourth portion 6 extends from the superior-medial part of the first portion 3. The fourth portion 3 forms a triangular part 12 defining a superior-medial corner of the prosthesis 1. For example, this corner may form an angle γ, as shown on FIG. 2A, ranging from about 100° to about 120°, preferably from about 105° to about 115°, for example of about 110°. The triangular part 12 allows the prosthesis 1 to provide an additional reinforcement in the medial superior area of the inguinal region. Such embodiments are particularly suitable when the hernia to be repaired is a direct inguinal hernia. The presence of the fourth portion 6 may also help the surgeon positioning optimally the prosthesis 1 by making the medial edge of the prosthesis 1 more visible to the surgeon. The surgeon may then more easily align the medial edge of the prosthesis 1 with the Linea Alba.

With reference to FIG. 4, one can see that the edge 7 extends in the three dimensions of the space. This allows the piece 2 to follow the anatomy of the region to be protected in an optimum way.

With reference to FIG. 2A, the edge 7 is provided with a reinforcement member 11.

The reinforcement member 11 forms a non-elastic belt maintaining the prosthesis 1 and helps the handling of the prosthesis 1 while providing a pop-up effect when the prosthesis 1 has been folded on itself, like in a trocar for example.

On FIG. 2A, the reinforcement member 11 runs along a part of the edge 7 while leaving free the medial inferior part of said edge 7. In particular, the reinforcement member 11 runs from a first end 11a, approximately located at the level of the central curve 9b, to a second end 11b, approximately located at the medial-inferior corner of the arched part 5, leaving free the medial inferior part of the edge 7. Such an embodiment, where the edge 7 is reinforced except in its medial inferior part, allows obtaining both the required pop-up effect for the deployment of the prosthesis 1 out of a trocar and the possibility to adapt and conform the third portion 5, namely the arched part 10, to the true anatomy of the medial inferior area of the inguinal region of the patient treated.

The four portions (3, 4, 5, 6) of the prosthesis 1 of FIG. 2A are made from a biocompatible material. The biocompatible material may comprise a bioresorbable, a non-bioresorbable material and mixtures thereof.

The four portions (3, 4, 5, 6) of the prosthesis 1 of FIG. 2A are preferably made from a porous textile, in particular a textile showing an elasticity allowing it to be deformed when submitted to an outer pressure and to come back to its initial predetermined three-dimensional shape when said outer pressure is released. Such a textile may for example be a porous knit made of polypropylene monofilament yarn having a diameter ranging from about 0.12 mm to about 0.25 mm, preferably from about 0.15 mm to about and 0.20 mm, for example of about 0.18 mm, and threaded one full one empty in two guide bars according to the following knitting pattern according to ISO 11676 standard, publication 2014: Bar I: 3-2/2-1/0-1//, Bar II: 0-1/1-2/3-2//. For example, the number of stitches per centimeter for such a porous knit may vary from about 7 to 15, preferably from about 10 to 12.

The reinforcement member 11 may be a fused part of the contour of the textile forming the piece 2, for example obtained by thermal welding. Such a fused part shows a smooth outer shape and is free of any traumatic element. Such a fused part also allows avoiding self-gripping of the textile when the prosthesis is folded on itself during its introduction to the implantation site via a trocar.

When the textile is a porous knit obtained from polypropylene monofilament as described above, the reinforcement member may be obtained by fusing the contour of the textile as follows: the contour of the textile is compressed between two jaws and heated to about 240° C. which is the melting point of polypropylene.

The piece 2 of the prosthesis 1 may be obtained using a compressive thermoforming process: for example, a flat textile such as the textile described above is secured between the two parts of a mold having the desired shape for the piece of the prosthesis to be obtained. The whole is heated at temperature of about 140° C. and then cooled down in order to obtain the preformed three-dimensional shaped piece 2. The preformed three-dimensional shaped piece thus obtained from said textile shows an elasticity allowing it to be deformed when submitted to an outer pressure and to come back to its initial predetermined three-dimensional shape when said outer pressure is released. Fusing the edge of the piece except for the medial inferior part of the edge allows forming a prosthesis capable of spreading out automatically from a trocar and having a good handleability, while showing in its medial inferior part an elasticity enabling the surgeon to conform the prosthesis to the medial inferior area of the inguinal region of the patient being treated.

The prosthesis of the invention is adapted to be used in the repair of inguinal hernia, such as the direct inguinal hernia, the indirect inguinal hernia and/or the femoral inguinal hernia. In particular, the prosthesis of the invention allows covering the medial inferior area of the inguinal anatomy, in particular the region around the upper part of the pubic bone, without having to tear or stretch the other parts of the prosthesis or to create additional folds likely to undesirably interfere with the surrounding organs.

What is claimed is:

1. A method of repairing a hernia in an inguinal region of a human body comprising:
    providing a prosthesis including a piece of biocompatible material having an initial preformed three-dimensional shape including a lateral side and a medial side extending along a medial-lateral axis and a superior side and inferior side extending along a superior-inferior axis, the piece including
        a first portion, configured to face an anterior abdominal wall, the first portion forming a partial spherical cap surface shaped and dimensioned to substantially conform to the anterior abdominal wall and including an inferior edge extending between the lateral and medial sides,
        a second portion, configured to face a psoas muscle, the second portion extending in an inferior direction from at least a lateral portion of the inferior edge of said first portion and forming a wavy-shaped wall, shaped and dimensioned to substantially conform to the psoas muscle, and
        a third portion forming an arched part, the arched part extending longitudinally substantially in the inferior direction from at least a medial portion of the inferior edge of the first portion, the arched part extending radially substantially in a front direction, the third portion configured to face the medial inferior area of an inguinal anatomy,
    applying pressure to the prosthesis to deform the prosthesis onto itself to form a deformed prosthesis,
    introducing the deformed prosthesis through a trocar to a site of implantation in the inguinal region of the human body,
    deploying the deformed prosthesis to return to the initial preformed three-dimensional shape, and
    positioning the prosthesis such that the third portion covers the medial inferior area of the inguinal anatomy.

2. The method of claim 1, wherein positioning the prosthesis further comprises positioning the first portion to face the anterior abdominal wall.

3. The method of claim 2, wherein positioning the prosthesis further comprises positioning the second portion to face the psoas muscle.

4. The method of claim 1, wherein positioning the third portion prosthesis includes positioning the third portion around an upper part of a pubic bone, without having to tear, stretch, or fold other portions of the prosthesis.

5. The method of claim 1, wherein positioning the prosthesis creates no tension in the prosthesis.

6. The method of claim 1, wherein the hernia in the inguinal region is selected from an indirect inguinal hernia, a direct inguinal hernia, or a femoral inguinal hernia.

7. The method of claim 1, wherein the method of repairing the hernia is performed by a transabdominal preperitoneal (TAPP) route.

8. The method of claim 1, wherein the method of repairing the hernia is performed by a totally extra-peritoneal (TEP) route.

9. The method of claim 1, wherein the initial preformed three-dimensional shape further defines an edge of the piece, the edge of the piece extending in three dimensions.

10. The method of claim 9, wherein the edge of the piece is provided with a reinforcement member at least on a part of a perimeter of the edge of the piece.

11. The method of claim 10, wherein a medial inferior part of the edge of the piece is free of any reinforcement member.

12. The method of claim 10, wherein the piece of biocompatible material comprises a textile.

13. The method of claim 12, wherein the reinforcement member comprises a fused part of a contour of the textile.

14. The method of claim 3, wherein the reinforcement member shows no elasticity along the perimeter of the edge of the piece.

15. The method of claim 1, wherein the piece of biocompatible material shows an elasticity allowing the piece to automatically return to the initial preformed three-dimensional shape when the pressure is released.

16. The method of claim 1, wherein the wavy-shaped wall includes a surface generated by a generatrix, under a form of a straight line, following a directrix, under a form of a directing curved line.

17. The method of claim 16, wherein the directing curved line includes at least a lateral curve extending substantially in the inferior direction and at least a central curve, offset in a medial direction with respect to the lateral curve, the central curve extending substantially in a superior direction.

18. The method of claim 17, wherein the directing curved line further includes a medial curve extending in the inferior direction.

19. The method of claim 1, wherein the piece further includes a fourth portion extending from a superior-medial part of the first portion, the fourth portion forming a triangular part defining a superior-medial corner of the prosthesis, the corner forming an angle ranging from about 100° to about 120°.

20. A method of repairing a hernia in an inguinal region of a human body comprising:
    deforming a prosthesis from an initial preformed three-dimensional shape to a deformed shape wherein the prosthesis is folded onto itself, the prosthesis including a piece of biocompatible material and the initial preformed three-dimensional shape including a lateral side and a medial side extending along a medial-lateral axis and a superior side and inferior side extending along a superior-inferior axis, the piece including
- a first portion, configured to face an anterior abdominal wall, the first portion forming a partial spherical cap surface shaped and dimensioned to substantially conform to the anterior abdominal wall and including an inferior edge extending between the lateral and medial sides,
- a second portion, configured to face a psoas muscle, the second portion extending in an inferior direction from at least a lateral portion of the inferior edge of said first portion and forming a wavy-shaped wall, shaped and dimensioned to substantially conform to the psoas muscle, and
- a third portion forming an arched part, the arched part extending longitudinally substantially in the inferior direction from at least a medial portion of the inferior edge of the first portion, the arched part extending radially substantially in a front direction, the third portion configured to face the medial inferior area of an inguinal anatomy, introducing the prosthesis in the deformed shape through a trocar to a site of implantation in the inguinal region of the human body, deploying the prosthesis to return to the initial preformed three-dimensional shape, and positioning the prosthesis such that the third portion covers the medial inferior area of the inguinal anatomy.

\* \* \* \* \*